(12) United States Patent
Ben-Haim et al.

(10) Patent No.: US 6,996,431 B2
(45) Date of Patent: *Feb. 7, 2006

(54) METHOD FOR ALIGNMENT OF BONE USING POSITION SENSORS

(76) Inventors: Shlomo Ben-Haim, 101 Yeffy Nof Avenue, Haifa 34454 (IL); Maier Fenster, 61 Brande Street, Petach Tikva 49600 (IL)

(*) Notice: Subject to any disclaimer, the term of this patent is extended or adjusted under 35 U.S.C. 154(b) by 425 days.

This patent is subject to a terminal disclaimer.

(21) Appl. No.: 10/314,729

(22) Filed: Dec. 9, 2002

(65) Prior Publication Data

US 2003/0139668 A1 Jul. 24, 2003

Related U.S. Application Data

(63) Continuation of application No. 09/381,753, filed as application No. PCT/IL98/00032 on Jan. 22, 1998, now Pat. No. 6,498,944, which is a continuation-in-part of application No. 08/595,365, filed on Feb. 1, 1996, now Pat. No. 5,738,096.

(51) Int. Cl.
*A61B 5/00* (2006.01)
(52) U.S. Cl. ...................... 600/407; 600/410; 600/425; 600/427
(58) Field of Classification Search ............... 600/407, 600/410, 411, 424, 425, 427, 437, 438, 473
See application file for complete search history.

(56) References Cited

U.S. PATENT DOCUMENTS

| | | | |
|---|---|---|---|
| 4,317,078 A | 2/1982 | Weed et al. | 324/208 |
| 5,279,309 A | 1/1994 | Taylor et al. | |
| 5,368,592 A | 11/1994 | Stern et al. | 606/33 |
| 5,370,692 A | 12/1994 | Fink et al. | 623/16 |
| 5,383,923 A | 1/1995 | Webster, Jr. | 607/125 |
| 5,391,199 A | 2/1995 | Ben-Haim | 607/122 |
| 5,404,297 A | 4/1995 | Birk et al. | 362/421 |
| 5,431,168 A | 7/1995 | Webster, Jr. | |
| 5,558,091 A | 9/1996 | Acker et al. | |
| 5,638,819 A | 6/1997 | Manwaring et al. | |
| 5,682,886 A | 11/1997 | Delp et al. | |
| 5,694,945 A | 12/1997 | Ben-Haim | |
| 5,752,513 A | 5/1998 | Acker et al. | |
| 6,470,207 B1 * | 10/2002 | Simon et al. | 600/426 |
| 6,498,944 B1 * | 12/2002 | Ben-Haim et al. | 600/407 |
| 2004/0059217 A1 * | 3/2004 | Kessman et al. | 600/424 |
| 2004/0181144 A1 * | 9/2004 | Cinquin et al. | 600/407 |

FOREIGN PATENT DOCUMENTS

| | | |
|---|---|---|
| WO | WO 94/04938 | 3/1994 |
| WO | WO 94/23647 | 10/1994 |
| WO | WO 96/05768 | 2/1996 |

* cited by examiner

*Primary Examiner*—Ruth S. Smith
(74) *Attorney, Agent, or Firm*—Louis J. Capezzuto (57) ABSTRACT

A method of measuring the size of an area (22) within a body, including bringing at least one position sensor (28) to each of a plurality of points in the area, determining position coordinates of the plurality of points, using the sensor (28) and calculating distances between the plurality of points.

51 Claims, 3 Drawing Sheets

METHOD FOR ALIGNMENT OF BONE USING POSITION SENSORS

RELATED APPLICATIONS

This application is a Continuation Application of U.S. patent application Ser. No. 09/381,753 filed on Apr. 13, 2000, now issued U.S. Pat. No. 6,498,944, which is the National Stage of International Application No. PCT IL98/00032 filed Jan. 22, 1998 which is a Continuation-in-Part Application of U.S. patent application Ser. No. 08/595,365 filed Feb. 1, 1996, now issued U.S. Pat. No. 5,738,096.

FIELD OF THE INVENTION

The present invention relates generally to the field of intrabody position determination, and specifically to intrabody measurements using position determination.

BACKGROUND OF THE INVENTION

There are many cases in which it is desired to measure organs or spaces within a patient's body. One such case is in preparation for organ transplantation. In transplantation procedures, in order to speed up the transplantation procedure and minimize the period in which the patient is without the transplanted organ, the new organ is preferably prepared before the transplantation procedure. In order to ensure proper reception of the new organ, it must be as similar as possible to the organ that is removed. In some organs the similarity in size may be approximate, since the surroundings of the organ are elastic. However, in other cases, the new organ must fit precisely in place of the old one.

In other cases, an empty space within a body is to be filled. For example, a patient may be missing a piece of a bone which is to be replaced by an artificial implant. Precise measurement of the space allows preparation of the artificial piece before its implantation, and may enable automatic fabrication of the artificial piece.

Measurements within a patient's body may be used also for other reasons, such as inspection and diagnosis. For example, in some cases, a tumor may be analyzed according to its size and/or its shape to track the progress of therapy or to plan a surgical operation. In tumor removal surgery, measurement of the tumor before, during, and after the surgery may be performed to verify removal of all or a desired portion of the tumor.

In the art, measuring an organ or a space within a body is usually performed on CT or NMRI images, or using ultrasound. U.S. Pat. No. 5,370,692 to Fink et al., which is incorporated herein by reference, describes a method of approximately fabricating prosthetic bone implants according to a CT image. However, these measurements are less accurate than direct measurements of the bone dimensions. In addition, some organs have a complicated geometry and therefore are hard to measure even on accurate images. Furthermore, some organs, such as the heart, are in movement and cannot be imaged fast enough to allow production of a clear and still image which can be measured.

There has been a system proposed for producing a prosthetic device, based on an arm which is connected through motion detectors to a model carver. A tip of the arm is moved on an outer surface of an organ, so as to produce a model of the organ. The use of such arms is limited to organs which are easily accessible to the arm, and therefore in most cases this system cannot be used in minimally invasive procedures. In addition, using more than one arm simultaneously is very difficult, since multiple arms interfere with each other.

When aligning bones, regions between bone fractures should be of minimal size, to ensure that the bone properly heals. Ordinarily, one or more X-ray images are taken of the broken bone, and the pieces are aligned accordingly. However, when the fracture is complicated, many images may be necessary, causing the surgeon and patient to be exposed to large amounts of radiation.

U.S. Pat. No. 5,558,091 describes a method of aligning sections of a broken bone, by observing a continually-updated image. The image is initially acquired using X-rays, but is then updated by computer image processing, based on a position determining system which tracks the movements of sensors attached to the bones. However, this method requires producing a separate sub-image for each bone section, and therefore is not suitable for multiple fracture pieces. Also, it would be useful to have a method of accurately realizing the proper alignment of the bones independent of the images.

SUMMARY OF THE INVENTION

It is an object of some aspects of the present invention to provide a method for accurate measurement of organs and spaces within a human body.

It is another object of some aspects of the present invention to provide a method of three-dimensional mapping of an organ situated within a human body.

It is a further object of some aspects of the present invention to provide a method for producing a three dimensional model of an organ which is situated within a human body.

Another object of some aspects of the present invention is to provide a method of aligning bone fractures without unduly exposing the patient and staff to large amounts of radiation.

Another object of some aspects of the present invention is to continuously report volumes or other sizes of regions between intrabody organs, such as bone fractures.

In some preferred embodiments of the present invention, one or more miniature position measuring sensors are placed at selected points within a patient's body. A position determining system, preferably situated outside the patient's body, determines the coordinates of the sensors.

Calculating circuitry associated with the position determining system calculates distances between the points, based on the coordinates. Thus, an organ can be measured by placing the sensors at extreme points of the organ and determining the coordinates of the points.

Preferably, the position determining system determines positions based on transmitting and detecting electromagnetic waves, and the sensors comprise miniature coils, in which currents flow responsive to the electromagnetic waves. Alternatively, the position determining system may operate using infrared or ultrasound waves or any other suitable non-ionizing fields, and the sensors accordingly comprise suitable transponders.

In some preferred embodiments of the present invention, position sensors are mounted onto or embedded within an object, for example, a screw, staple, electrode or shunt, which is implanted in the body. The position sensors may be used both for guiding the object into the body, and later on for measurement of intrabody spaces that the object adjoins.

In some preferred embodiments of the present invention, the sensors are placed at a plurality of points on an outer or inner surface of an organ, while the position determining system continuously determines and records the coordinates of these points, preferably at a high sampling rate. The calculating circuitry calculates the size of the organ according to the recorded coordinates. Preferably, the sensors are mounted on the tip of one or more catheters, so as to allow easy movement of the sensors along the surface of the measured organ.

In some preferred embodiments of the present invention, one or more reference sensors are placed within the patient's body for use in making an intrabody measurement. These reference sensors are fixed in place by an operator of the catheter, for example, by a surgeon and are substantially not moved thereafter, during the measurement. The reference sensors are preferably fixed to one of the patient's organs, such as the heart, so that the movements of the reference sensors follow the movements of the patient or of the organ. The coordinates of the reference sensors are determined by the position determining system and are used by the calculating circuitry to transform the (time-varying) coordinates of the recorded points to a stationary coordinate system. Preferably, for each point that is recorded, the position determining system determines simultaneously the coordinates of the measuring position sensor and of at least one of the reference sensors. The calculating circuitry transforms the coordinates of the point to a frame of reference that is fixed to the moving organ.

Preferably, measurement of the organ is performed using a catheter, which may be inserted into the patient for other purposes, as well. In a preferred embodiment of the present invention, a heart valve is examined using a measuring catheter, before and after a valve replacement procedure. Preferably, the valve is replaced in a minimally-invasive procedure, using, for example, the Port-Access™ MVR system, supplied by Heartport Inc. The position information determined during the examination before the replacement procedure is used to provide an accurate measurement of the valve for the purpose of preparing a suitable prosthesis.

In order to perform the measurement, a catheter with one or more position sensors mounted on its tip is inserted into the patient's heart and brought into proximity with the valve. The catheter preferably also includes a flow or pressure sensor, which is used for determining rates of blood flow through and in the vicinity of the valve, at a plurality of time points. The surgeon may determine accordingly the blood flow pattern in the vicinity of the valve. Preferably, the surgeon also correlates the flow information with the valve state, i.e., when the valve is open and when it is closed. The valve state is determined, for example, by fixing a position sensor to the valve and allowing the sensor to drift freely with the valve, while the position determining system determines the sensor's position. Preferably, the position sensor is detachable from the catheter, so that the catheter may place the sensor and then move on to other positions in which the flow or pressure is to be measured, simultaneously with determining the state of the valve. The detachable sensor may either be connected through signal wires to the catheter or be a wireless position sensor. The surgeon uses the information thus gathered in deciding whether to replace the valve.

If the valve is to be replaced, it is immediately measured, preferably using the catheter already in the heart, so that a replacement valve of the same size can be prepared. During measurement, the tip of the catheter is systematically brought into contact with a plurality of points on the circumference of the valve, in order to determine a plurality of points forming a map of the valve. The number of points to be determined depends on the desired accuracy of the valve size measurement.

In order to compensate for changes in position of the measuring catheter due to the movements of the heart, a reference catheter, with one or more reference position sensors, is preferably placed at a fixed point on or, preferably, within the heart. For each point touched by the measuring catheter's tip, the position determining system records the position of the tip, and simultaneously, the position of the reference catheter. The calculating circuitry receives the positions of the determined points and compares the position of the measuring catheter relative to the reference catheter, so as to map the points contacted by the measurement catheter in a frame of reference fixed to the heart. According to these calculations a map of the valve is produced.

Preferably, a parameter characteristic of the tissue adjacent each recorded point is also determined, so as to ascertain whether the point is actually on the valve. This parameter may be, for example, the local electric activity, since the electrical activity of heart muscle tissue is substantially greater than that in the valve.

The accuracy of the map depends on the number of points on the valve which are recorded. If not enough points were recorded in order to produce a map of satisfactory point density, the calculating circuitry preferably prompts the operator to measure additional points. After the circumference of the valve is properly mapped, the calculating circuitry preferably reports the size and volume of the valve.

According to the map and reported size, a new valve, preferably a flexible valve which is inserted using a minimally invasive method, is prepared for implantation. Preferably a catheter with a position sensor is also used during the implantation procedure, to locate points which were mapped earlier. The surgeon can use these points as a reference, to assist him in accurately inserting the new valve into its place. After the implantation, the catheter is preferably used again to check whether the new valve operates properly, in a manner similar to the diagnostic tests performed before the implantation.

In other preferred embodiments of the present invention, position sensors are used in measuring and aligning bone fractures, generally in order to minimize the distance and/or space between pieces of fractured bone that are being fixed. Position sensors are fixed to each of the pieces of the fractured bone, using screws, adhesive or any other suitable connection method.

In order to calibrate the sensors before beginning the fixation, the region of a fracture is imaged using any suitable imaging method known in the art, such as fluoroscopy or MRI. Simultaneously, position coordinates of the sensors are determined and recorded using the position determining system. An image, preferably a three dimensional image, of the fracture pieces is displayed on a screen. The position coordinates of the sensors are registered with specific points in a coordinate frame associated with the image, and the contours of each piece are linked with the respective sensor. Preferably, each point in the image which represents part of a fracture piece is linked with one of the sensors. When the fracture pieces are moved, the display on the screen is updated according to the position coordinates of the sensors, which are updated continuously by the position determining system. Thus an on-line image of the bone fracture is produced, enabling easy alignment of the fracture, without requiring additional imaging.

In one of these preferred embodiments, during calibration, which is preferably performed after the patient's skin covering the bone is surgically opened, an external probe with a position sensor at its tip is passed over the surface of the fracture pieces. The position determining system determines and records the positions of a plurality of points on the surface of each piece, using the sensor within the tip of the external probe. The points on the surface of each piece are preferably registered relative to the sensor connected to the piece, so as to compensate for movements of the piece during calibration. Thus, for each fracture piece, the calculating circuitry records the coordinates of the sensor connected to the piece and coordinates of the plurality of points received during calibration, so that the position and shape of the entire piece can be determined based on the position and orientation of the position sensor fixed thereto. During alignment of the bone, the image of the bone is thus precisely updated.

In some of these preferred embodiments, the circuitry produces and updates an estimate of the distance and/or volume between the fracture pieces, based on the position coordinates of the sensors. To calculate the distance from a piece to its neighboring pieces, the calculating circuitry preferably finds for each of the plurality of points on the piece the closest determined point which is not on the same piece. The distance to this closest point is used to estimate the distance and volume between the pieces.

When the volume is smaller than a predefined value, the calculating circuitry preferably signals the surgeon that the pieces are properly aligned. Alternatively, when the volume cannot be reduced to within the predefined value, the calculating circuitry may be used to report the dimensions of the region, so that a prosthetic implant can be fabricated accordingly. After the bone is properly aligned, the sensors may be removed from the bone.

In a further preferred embodiment of the present invention, the calculating circuitry is coupled to modeling apparatus which automatically fabricates the prosthetic bone implant.

In another preferred embodiment of the present invention, sensors are connected to vertebrae of the spine during back surgery. The distances between the sensors are constantly reported to the surgeon, who accordingly aligns the vertebrae.

There is therefore provided in accordance with a preferred embodiment of the present invention, a method of measuring the size of an area within a body, comprising bringing at least one position sensor to each of a plurality of points in the area, determining position coordinates of the plurality of points, using the sensor, and calculating distances between the plurality of points.

Preferably, bringing the at least one sensor to the plurality of points comprises bringing the distal end of a probe with the at least one sensor mounted thereon into contact with each of the plurality of points.

Preferably, bringing the distal end into contact with each of the plurality of points comprises passing the distal end over a surface adjacent the area.

Preferably, bringing the at least one sensor to each of the plurality of points comprises bringing the at least one sensor to a plurality of points within an organ.

Alternatively or additionally, bringing the at least one sensor to the plurality of points comprises bringing the at least one sensor to a plurality of points on the circumference of an organ.

Alternatively or additionally, bringing the at least one sensor to the plurality of points comprises bringing the at least one sensor to a plurality of points on one or more pieces of a fractured bone.

Preferably, determining the positions of the points comprises transmitting and receiving magnetic fields.

Preferably, the method includes constructing a geometrical map of the plurality of points.

Preferably, the method further includes displaying the map in conjunction with a three dimensional image of a corresponding portion of the body.

Preferably, the method includes calculating a volume associated with the area.

Preferably, the method includes producing a model of the area based on the distances.

Preferably, the method includes identifying a region of the area in which there is less than a predetermined density of determined points, and prompting a user to bring a sensor to the region to determine coordinates of additional points.

In some preferred embodiments of the present invention, the area is in motion, and the method includes associating at least one reference sensor with the area, so that the reference sensor moves with the area determining the position of the reference sensor when the position of a point is determined, and comparing the positions of the plurality of points to the position of the reference sensor, so as to transform the positions to a substantially stationary frame of reference.

Preferably, bringing the position sensor to each of a plurality of points comprises bringing the position sensor to a plurality of points in a patient's heart.

Preferably, the method includes measuring a physiological parameter at the plurality of points, indicative of whether the point belongs to the area to be measured.

Preferably, measuring the physiological parameter comprises measuring an electrical activation signal at the plurality of points.

There is further provided in accordance with a preferred embodiment of the present invention, a method of aligning pieces of a fractured bone, comprising uniquely associating an anchor point with each of the pieces, determining for each piece coordinates of a plurality of points, which are descriptive of the shape and position of the piece relative to the anchor point, moving the pieces so as to align the bone based on the shapes and positions of the pieces, repeatedly determining coordinates of the anchor points while moving the pieces, and updating position information regarding the pieces, based on the coordinates of the anchor points, for guidance in moving the pieces.

Preferably, determining the coordinates comprises transmitting and receiving magnetic fields.

Preferably, uniquely associating an anchor point comprises fixing one or more sensors to each of the pieces.

Preferably, updating the position information comprises calculating a distance between two pieces.

Preferably, the method includes notifying a user when the distance between two pieces is smaller than a predetermined distance.

Preferably, updating the position information comprises calculating the volume of an area between two pieces.

Preferably, the method includes notifying a user when the volume is smaller than a predetermined value.

Preferably, the method includes producing an image of the pieces and updating the image based on the updated position information.

Preferably, producing an image of the pieces comprises producing a three-dimensional image of the pieces.

Preferably, the method includes producing a model of a volume between two pieces.

There is further provided in accordance with a preferred embodiment of the present invention, apparatus for intrabody measurement of an area within a body, comprising a probe for insertion into the area, a position sensor mounted on the probe, a position determining system, which determines position coordinates of the sensor at a plurality of points adjacent the area, and calculating circuitry, which calculates distances between the plurality of points.

Preferably, the position determining system determines the coordinates by transmitting and receiving magnetic fields.

Preferably, the apparatus includes a screen for displaying a geometrical map of the plurality of points based on the coordinates.

Preferably, the calculating circuitry calculates a volume of the area.

Preferably, the apparatus includes a modeling machine, coupled to the calculating circuitry, which produces a model of the area responsive thereto.

Preferably, the circuitry calculates a density of the plurality of points and signals a user as to areas in which the density is below a predetermined limit.

Preferably, the area is in motion, and the apparatus comprises a reference catheter, including a reference sensor, wherein the position determining system determines position coordinates of the reference sensor when determining the coordinates of the plurality of points, and the calculating circuitry compares the coordinates of the plurality of points to the coordinates of the reference sensor, so as to transform the coordinates of the points to an inert frame of reference.

Preferably, the probe comprises a flexible catheter for insertion into a patient's heart.

Preferably, the catheter comprises an electrode for measuring electrical activity at the plurality of points.

There is further provided in accordance with a preferred embodiment of the present invention, apparatus for aligning pieces of a fractured bone, comprising a plurality of bone position sensors, which are connected to corresponding pieces, a position determining system for determining positions of the sensors, a probe, including a probe position sensor, which is passed over a plurality of points on the surface of one or more of the pieces, wherein the position determining system determines coordinates of the plurality of points, representative of the shapes of the pieces, and calculating circuitry, which determines and updates the coordinates of the plurality of points on the pieces, responsive to movements of the bone position sensors.

Preferably, the apparatus includes an imaging device for producing an image of the pieces, wherein the coordinates of the plurality of points are registered with the image.

There is further provided in accordance with a preferred embodiment of the present invention, apparatus for aligning pieces of a fractured bone, comprising a plurality of position sensors, which are fixed to corresponding ones of the pieces, an imaging device, which produces an image of the pieces, a position determining system, which determines position coordinates of the sensors, and calculating circuitry, which associates each piece seen in the image with its respective position sensor and updates the positions of the pieces in the image, responsive to changes in the coordinates of the sensors.

Preferably, the calculating circuitry automatically associates the image of each piece with its respective position sensor according to attributes of the image of the piece.

Preferably, the calculating circuitry associates the image of each piece with its respective position sensor according to information received from a user.

Preferably, the circuitry produces a geometrical map, based on the coordinates, which is displayed along with the images of the fractures.

Preferably, the position determining system determines positions by transmitting and receiving non-ionizing fields.

Preferably, the position determining system determines positions by transmitting and receiving magnetic fields.

Preferably, the calculating circuitry calculates distances between pieces.

Alternatively or additionally, the calculating circuitry calculates volumes between the pieces.

Preferably, the apparatus includes a modeling machine, coupled to the calculating circuitry, which produces a model of an area between the pieces responsive to the circuitry.

Preferably, the plurality of position sensors are mounted on screws, which are screwed into the pieces.

The present invention will be more fully understood from the following detailed description of the preferred embodiments thereof, taken together with the drawings, in which:

DETAILED DESCRIPTION OF PREFERRED EMBODIMENTS

Figure 1:
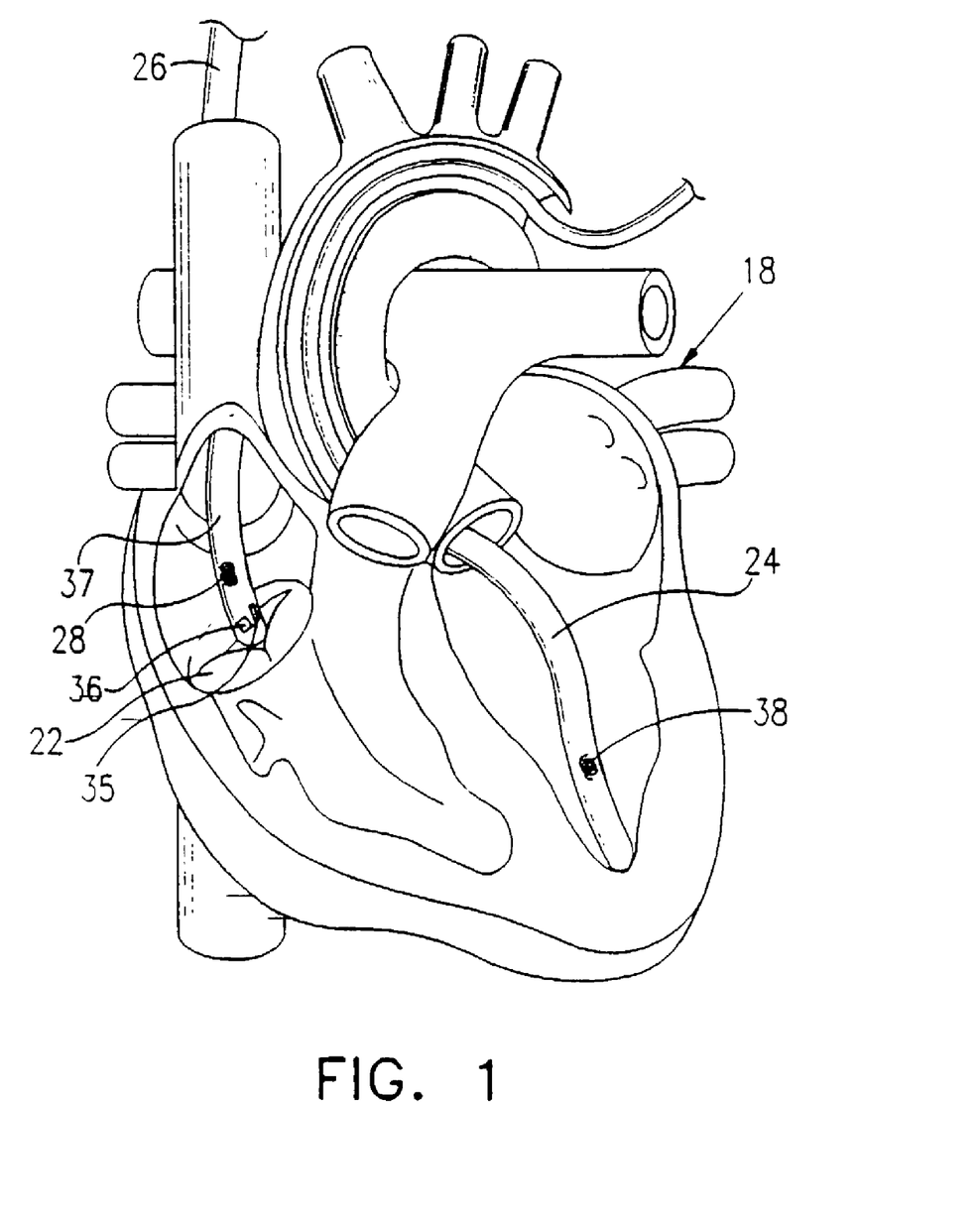
FIG. 1 is a perspective view of a patient's heart with a measuring catheter, in accordance with a preferred embodiment of the present invention.

FIG. 1 shows a patient's heart 18 with a tricuspid valve 22 therein, which is measured in accordance with a preferred embodiment of the present invention. A measurement catheter 26 is situated within the patient's heart near valve 22. A reference catheter 24, comprising a position sensor 38, is situated at a fixed point relative to heart 18, preferably at the apex thereof, such that the movements of catheter 24 coincide with the movements of heart 18.

Catheter 26 is preferably thin and durable and is suitable for insertion into and maneuvering within the patient's heart. Such catheters are described, for example, in PCT patent application US95/01103 and in U.S. Pat. Nos. 5,404,297, 5,368,592, 5,431,168, 5,383,923, the disclosures of which are incorporated herein by reference. Preferably, catheter 26 comprises a pressure sensor 36, at least one position sensor 28, and one or more working channels 37 which allow attachment of catheter 26 by suction to points within heart 18. Such suction allows connection of catheter 26 to valve 22 in order to follow the movements of the valve. Preferably, channels 37 are connected to a suction device (not shown), such as a pump, at the proximal end of the catheter.

Figure 2:
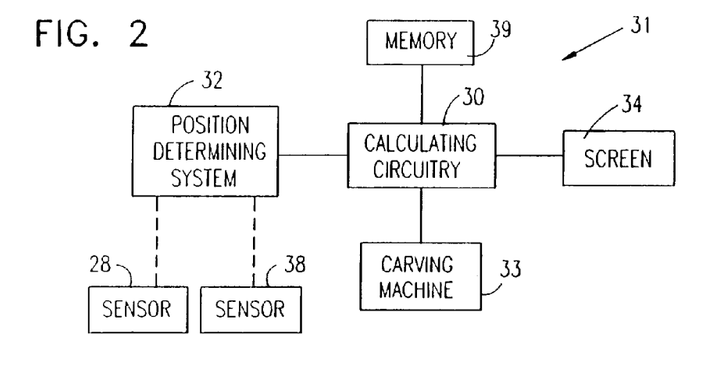
FIG. 2 is a block diagram of measuring apparatus in accordance with a preferred embodiment of the present invention.

FIG. 2 is a block diagram showing measuring apparatus 31 used to measure heart valve 22, in accordance with a preferred embodiment of the present invention. A position determining system 32 determines coordinates of sensors 28 and 38, preferably by transmitting and/or receiving magnetic waves to or from the sensors, as described, for example, in PCT publications PCT/GB93/01736, WO94/04938, and WO96/05768, in U.S. Pat. No. 5,391,199, or in PCT application PCT/IL97/00009, which is assigned to the assignee of the present application, all of which are incorporated herein by reference. Sensors 28 and 38 preferably comprise miniature coils.

Preferably, the coordinates determined by position determining system 32 are stored in a memory 39 for further use. Calculating circuitry 30 receives the determined coordinates and, based thereon, calculates the size of intrabody regions. Circuitry 30 preferably is also connected to a display screen 34, on which images and/or geometrical maps of intrabody regions may be displayed.

Pressure sensor 36 is preferably located adjacent the distal tip of catheter 26, as shown in FIG. 1. The relative blood flow at a point within the heart may be determined according to the pressure measured at the point, as is known in the art. Alternatively or additionally, a flow sensor at the tip of the catheter, for example, based on a Doppler ultrasound transducer, is used to directly measure the blood flow.

Preferably, an image of heart 18 along with catheter 26 is produced, before diagnosing the condition of valve 22. The image is preferably a three-dimensional image, produced using any suitable method known in the art, such as CT or MRI. Preferably, the image is displayed on screen 34 and is associated with a geometrical map based on the determined position coordinates of the catheter. Preferably, during further procedures, the geometrical map is continually updated, and circuitry 30 updates the image on screen 34 accordingly.

Catheter 26 is used to diagnose the functionality of valve 22, in order to allow a surgeon to decide whether valve 22 needs to be replaced. The condition of valve 22 is diagnosed by measuring the blood flow at points in the proximity of valve 22, in different states of the valve. Catheter 26 is temporarily fixed to valve 22, preferably using suction through channel 37, or any other suitable method known in the art, and then drifts freely according to the movements of the valve. Position determining system 32 determines and, preferably, maps or plots the pattern of movement of valve 22. According to these movements, a surgeon can observe whether valve 22 is in an open or closed state, and can track the motion of the valve.

Alternatively, a separate position sensor, preferably based on a wireless transponder, as is known in the art, is attached to valve 22, thus allowing catheter 26 to be moved elsewhere, while the movements of valve 22 and of the separate sensor attached thereto are determined by position determining system 32. The surgeon can thus correlate between the state of valve 22 and the flow at points near valve 22, to determine whether valve 22 is functioning properly. Alternatively, the surgeon can determine the state of valve 22 solely according to the time pattern of the flow through valve 22.

The surgeon then decides according to the flow information whether to replace valve 22.

If valve 22 is to be replaced, it is preferably immediately measured, and a map of the valve is preferably produced in order to prepare a replacement valve of proper size.

Preferably, catheter 26 is brought systematically to a plurality of points in the proximity of valve 22, to produce a map of the valve. The position of each point is measured using position sensor 28, preferably along with a parameter characteristic of the adjacent tissue material, indicating whether the position belongs to heart muscle or to the valve, as described below. The position measurements are referred by circuitry 30 to the position of reference catheter 24, in order to compensate for changes in the position of catheter 26 due to the movements of heart 18. Preferably, the parameter characteristic of the tissue is determined according to electrical activation signals received from the adjacent tissue, using an electrode 35. The heart's muscle tissue is generally characterized by electrical activation signals that pass through it, whereas the fibrous tissue of the valve has no electrical activation. Therefore, a map of valve 22 is determined by noting points which show little or no electrical activity.

Based on the map, circuitry 30 preferably calculates and reports the dimensions of valve 22. Preferably, circuitry 30 produces a reconstructed three dimensional map of valve 22, which is displayed on screen 34.

In a preferred embodiment of the present invention, the surgeon may request that the map have at least a minimal density of determined points. Circuitry 30 preferably notifies the surgeon of areas that do not have enough determined points, according to the surgeon's requirement. In addition, the surgeon may decide independently, based on the display on screen 34, to determine additional points in an area of valve 22. The surgeon accordingly moves the catheter tip through such areas to determine additional points. The display on screen 34 is updated to include the newly determined points.

In preferred embodiments of the present invention, circuitry 30 may be connected to various types of ancillary apparatus, such as a model carving machine 33, which carves a model of valve 22 based on the map. The carved model can be used to choose and/or fabricate the new valve.

Preferably, the old valve is removed and the new valve is inserted by means of an endoscopic or other minimally invasive procedure. The endoscope preferably includes position sensors so that the surgeon can direct the endoscope to points determined during the measuring procedure. Thus, the new valve is inserted precisely to the points from which the deteriorated valve was taken. Alternatively, a position sensor is connected to the valve to allow accurate positioning of the valve within the heart. After the insertion procedure, the operation of the new valve is preferably checked in the same manner as the deteriorated valve was checked.

Figure 3:
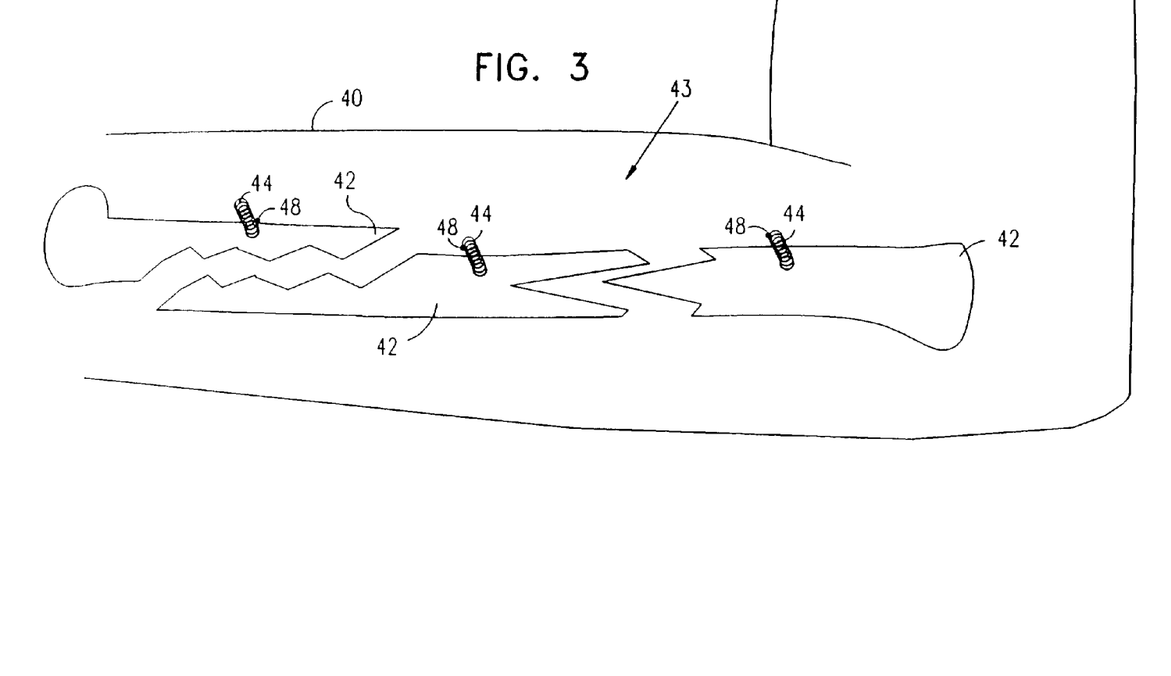
FIG. 3 is a side cross sectional view of an arm with a fractured bone which is aligned in accordance with a preferred embodiment of the present invention.

FIG. 3 shows a fractured bone 43 which is aligned in accordance with a preferred embodiment of the present invention. A patient's arm 40 has been opened in order to align pieces 42 of bone 43. Preferably, one or more sensors 44, preferably comprising coils, as described above, are fixed to each of pieces 42. Sensors 44 serve as anchor points which indicate the positions of their respective fracture piece. In order to track the position of a piece it is sufficient to track the anchor point and update the positions of other points on the piece according to their positions relative to the anchor point. Sensors 44 are preferably screwed into pieces 42. Alternatively or additionally, sensors 44 are fixed to pieces 42 using a clamp, a staple, an adhesive or any other suitable connection mechanism.

After sensors 44 are fixed to pieces 42, an X-ray or CT image of pieces 42 is preferably produced and displayed on screen 34. Simultaneously, the positions of sensors 44 are preferably determined by a position determining system 32. The position determining system is preferably calibrated by circuitry 30 with respect to the image, as will now be described.

In order for circuitry 30 to associate the determined positions of sensors 44 with their respective images, the surgeon is preferably prompted to point to each of sensors 44. Preferably, sensors 44 have associated fiducial marks 48, which appear clearly on the image and thus simplify identification of sensors 44 on the image. If a CT imaging system is used, fiducial marks 48 preferably comprise a radiopaque substance, such as aluminum. Alternatively, circuitry 30 automatically recognizes sensors 44 according to their shape and/or their computed density.

In addition, the surgeon preferably associates each piece 42 with its respective one or more sensors 44 by pointing on the image to each of pieces 42, along with its one or more respective sensors 44. Preferably, the outer surfaces or outlines of pieces 42 are also pointed out to circuitry 30, to enhance the accuracy of the identification of pieces 42. Alternatively or additionally, circuitry 30 may be programmed to automatically recognize pieces 42 according to their shape and/or their computed density.

Alternative methods of associating between X-ray images and coordinates of position sensors therein are described in U.S. Provisional Patent Application No. 60/042,873, filed Mar. 31, 1997, which is assigned to the assignee of the present invention and is incorporated herein by reference.

Figure 4:
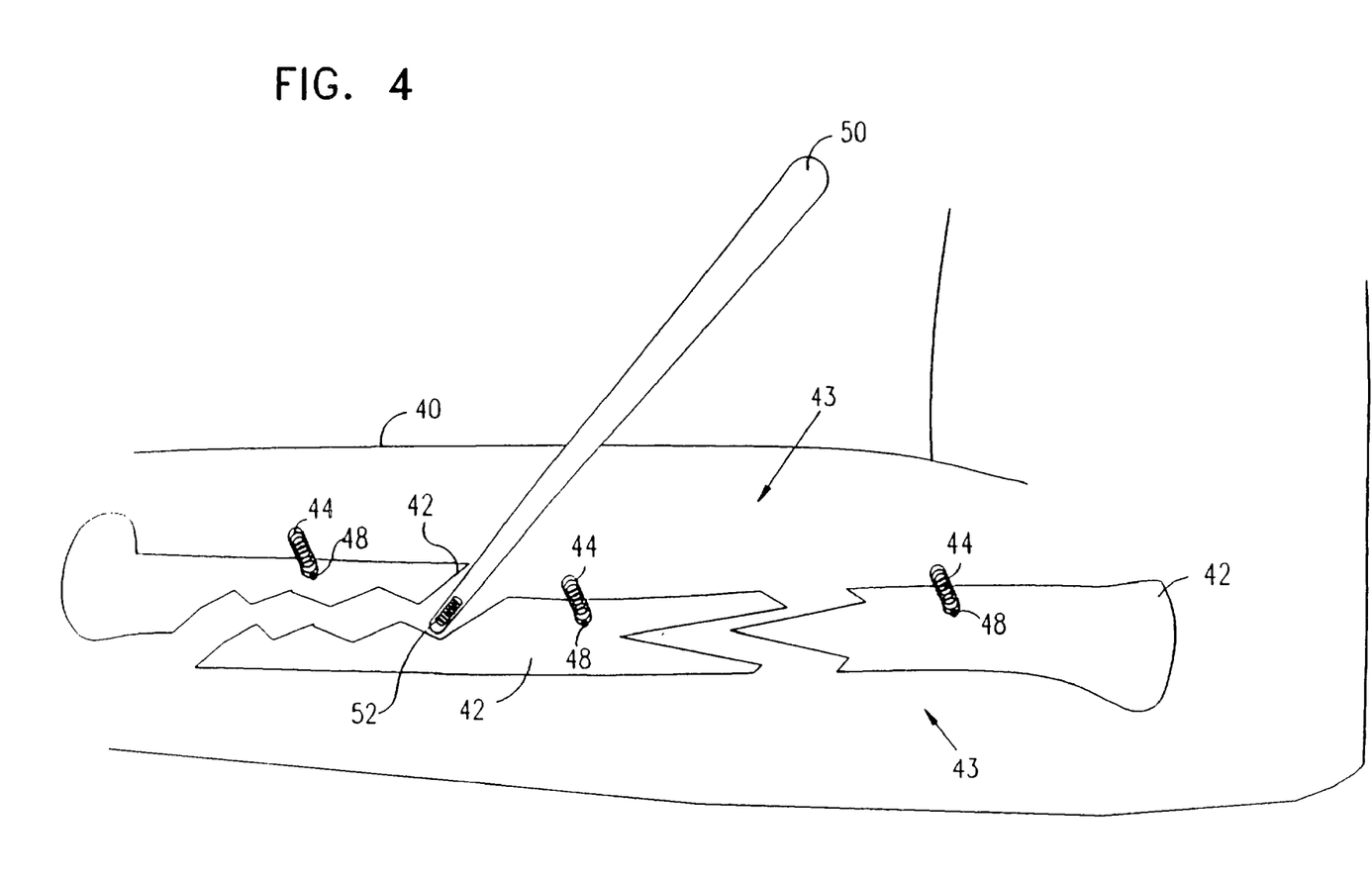
FIG. 4 is a schematic view of an arm with a fractured bone which is aligned in accordance with another preferred embodiment of the present invention.

FIG. 4 shows another method for pointing out pieces 42, in accordance with a preferred embodiment of the present invention. A probe 50, with a position sensor 52 mounted on its tip, is passed over the surfaces of pieces 42 through an incision in the skin of arm 40. Position determining system 32 determines points on the surfaces of pieces 42, preferably at a high sampling rate, and thus the shape of pieces 42 is accurately determined by circuitry 30. Preferably, circuitry 30 notifies the surgeon of areas on the surface of pieces 42 which do not have a sampled point density above a predetermined value. The surgeon accordingly will pass probe 50 over these areas in order to achieve the required point density.

After calibration, the surgeon moves pieces 42 in an attempt to properly align bone 43. As pieces 42 are moved, the image on screen 34 is preferably updated, based on position measurements by sensors 44, thus aiding the surgeon in aligning pieces 42. Preferably, more than one view of pieces 42 is displayed on screen 34. Bone 43 may be aligned using holding apparatus for keeping the fracture pieces fixed in place, as described for example in U.S. Pat. No. 5,279,309 which is incorporated herein by reference.

In a preferred embodiment of the present invention, circuitry 30 continuously reports the distances between the pieces. In addition, circuitry 30 may continuously calculate the volume remaining between each two adjacent pieces 42, based on the distance therebetween and the surface areas of the pieces, determined in the measurement procedure described above. Preferably, when the distance or volume are beneath a predetermined value, circuitry 30 signals the surgeon that the pieces are properly aligned.

In cases in which the surgeon observes that pieces of bone 43 are missing, or otherwise cannot be perfectly aligned, circuitry 30 enables easy fabrication of prosthesis. After the surgeon aligns pieces 42 as well as possible, the surgeon actuates circuitry 30, to calculate the volume and dimensions of empty areas between pieces 42. Alternatively or additionally, maps of these areas are produced. Based on the calculated volumes, the surgeon decides whether artificial implants are to be used to fill the empty areas. Preferably, a model of the area to be filled or a bone prosthesis is automatically produced by carving machine 33 or other machinery coupled to circuitry 30.

It will be appreciated that although the above embodiment has been described with reference to aligning bone pieces following a fracture of the arm, the principles of the present invention may be used to measure and align any rigid fragments within a body, such as the vertebrae. A position sensor is preferably connected to each vertebra, and the distance between the vertebrae is reported by the circuitry.

It will further be appreciated that although the above preferred embodiments are described as using magnetic field-based position determining systems, the principles of the present invention may be applied using any suitable position determining system known in the art, for example, an ultrasonic system.

It will be appreciated that the preferred embodiments described above are cited by way of example, and the full scope of the invention is limited only by the claims.

What is claimed is:

1. A method for alignment of pieces of bone comprising the steps of:
   fixing a sensor to each piece of bone;
   producing an image of the pieces of bone;
   determining the position of each sensor using a position determining system;
   associating the determined position of each sensor with the image; and
   aligning the pieces of bone based on the determined position of each sensor associated with the image.

2. The method according to claim 1, further comprising implanting an object at each piece of bone.

3. The method according to claim 2, further comprising mounting a sensor to the object.

4. The method according to claim 3, wherein the object is a prosthesis.

5. The method according to claim 1, wherein the sensor is fixed to each piece of bone using a connection mechanism.

6. The method according to claim 5, wherein the connection mechanism is a clamp.

7. The method according to claim 5, wherein the connection mechanism is a staple.

8. The method according to claim 5, wherein the connection mechanism is an adhesive.

9. The method according to claim 1, wherein the image is a three dimensional image.

10. The method according to claim 9, wherein the image is obtained using fluoroscopy.

11. The method according to claim 9, wherein the image is obtained using MRI.

12. The method according to claim 9, wherein the image is obtained using X-Ray.

13. The method according to claim 9, wherein the image is obtained using CT.

14. The method according to claim 9, wherein the image is displayed on a screen.

15. The method according to claim 1, wherein the sensor saves as an anchor point.

16. The method according to claim 1, wherein the position determining system uses non-ionizing fields.

17. The method according to claim 16, further comprising using electromagnetic waves to determine the position of each sensor.

18. The method according to claim 17, wherein the sensor comprises at least one coil.

19. The method according to claim 16, further comprising using ultrasound to determine the position of each sensor.

20. The method according to claim 19, wherein the sensor comprises a transponder.

21. The method according to claim 16, further comprising using infrared to determine the position of each sensor.

22. The method according to claim 1, wherein the pieces of bone comprise rigid fragments.

23. The method according to claim 22, wherein the rigid fragments are vertebrae of the spine.

24. The method according to claim 1, further comprising fixing the sensor to each piece of bone by screwing the sensor into the piece of bone.

25. The method according to claim 1, wherein the pieces of bone are pieces of fractured bone.

26. A method for alignment of pieces of bone comprising the steps of:
fixing at least one sensor to each piece of bone;
determining position coordinates of the at least one sensor on each piece of bone;
determining position coordinates of a plurality of points for each piece of bone;
determining a shape and position of each piece of bone based on the position coordinates of the plurality of points and the at least one sensor fixed thereto;
determining position coordinates of the at least one sensor for each piece of bone while moving the pieces of bone;
updating the position coordinates of the plurality of points for each piece of bone based on the position coordinates of the at least one sensor determined while moving the pieces of bone; and
using the updated position coordinates of the plurality of points and the position coordinates of the at least one position sensor as guidance for moving the pieces of bone.

27. The method according to claim 26, further comprising using an external probe with a position sensor at a tip of the probe for determining position coordinates of the plurality of points for each piece of bone.

28. The method according to claim 26, further comprising using a three-dimensional image associated with the position coordinates of the at least one sensor and the plurality of points for each piece of bone.

29. The method according to claim 28, wherein the image is displayed on a screen.

30. The method according to claim 28, wherein the image is obtained using fluoroscopy.

31. The method according to claim 28, wherein the image is obtained using MRI.

32. The meted according to claim 28, wherein the image is obtained using X-Ray.

33. The method according to claim 28, wherein the image is obtained using CT.

34. The method according to claim 26, further comprising implanting an object at the pieces of bone.

35. The method according to claim 34, further comprising mounting a sensor to the object.

36. The method according to claim 35, wherein the object is a prosthesis.

37. The method according to claim 26, wherein the at least one sensor is fixed to each piece of bone using a connection mechanism.

38. The method according to claim 37, wherein the connection mechanism is a clamp.

39. The method according to claim 37, wherein the connection mechanism is a staple.

40. The method according to claim 37, wherein the connection mechanism is an adhesive.

41. The method according to claim 26, wherein the at least one sensor serves as an anchor point.

42. The method according to claim 26, further comprising using a position determining system having non-ionizing fields.

43. The method according to claim 42, further comprising using electromagnetic waves for determining position coordinates of the at least one sensor and the plurality of points for each piece of bone.

44. The method according to claim 43, wherein the at least one sensor comprises at least one coil.

45. The method according to claim 42, further comprising using ultrasound for determining position coordinates of the at least one sensor and the plurality of points for each piece of bone.

46. The method according to claim 45, wherein the at least one sensor comprises a transponder.

47. The method according to claim 42, further comprising using infrared for determining position coordinates of the at least one sensor and the plurality of points for each piece of bone.

48. The method according to claim 26, wherein the pieces of bone comprise rigid fragments.

49. The method according to claim 48, wherein the rigid fragments are vertebrae of the spine.

50. The method according to claim 26, further comprising fixing the at least one sensor to each piece of a bone by screwing the at least one sensor into the piece of bone.

51. The method according to claim 26, wherein the pieces of bone are pieces of fractured bone.

* * * * *